United States Patent [19]

Sanchez et al.

[11] Patent Number: 5,006,471
[45] Date of Patent: Apr. 9, 1991

[54] FUNGAL RESISTANCE MARKERS

[75] Inventors: Florentina S. Sanchez; Victor R. Susan; Laura Carramolino-Fitera; Agustin P. A. Ortega, all of Madrid, Spain

[73] Assignee: Antibioticos S.A. of Bravo Murillo 38, Madrid, Spain

[21] Appl. No.: 32,065

[22] Filed: Mar. 26, 1987

Related U.S. Application Data

[63] Continuation of Ser. No. 9,713, Feb. 2, 1987.

[30] Foreign Application Priority Data

Mar. 26, 1986 [GB] United Kingdom ............... 8607502

[51] Int. Cl.$^5$ .............. C12N 1/15; C12N 15/11; C12N 15/80; C12Q 1/04
[52] U.S. Cl. ................. 435/254; 435/34; 435/91; 435/171; 435/172.1; 435/172.3; 435/320.1; 435/911; 435/933; 435/935; 536/27; 935/6; 935/9; 935/10; 935/11; 935/14; 935/22; 935/23; 935/24; 935/27; 935/55; 935/59; 935/68
[58] Field of Search ............ 435/34, 91, 171, 172.1, 435/172.3, 254, 320, 911, 933, 935; 536/27; 935/6, 9, 10, 11, 14, 22, 23, 24, 27, 55, 56, 59, 60, 66, 68

[56] References Cited

U.S. PATENT DOCUMENTS 4,775,624 10/1988 Bang et al. ............... 435/226
4,792,520 12/1988 Stambrook et al. ........... 435/6

OTHER PUBLICATIONS

Yelton et al., Genetics, 81:1470-74 (1984).
Vara et al., "Cloning and Expression of a Puromycin N-Acetyl Transferase Gene From *Streptomyces alboniger* in *Streptomyces lividans* and *Escherichia coli*", Gene. 33: 197-206 (1985).
The Merck Index, pp. 925-926, 1146.
The Pharmacological Basis of Therapeutics, pp. 1178-1180.
Genetics, A Molecular Approach, Mays, pp. 403-411.
Principles of Biochemistry, White, pp. 848-892.
Vara et al., "Expression in Mammalian Cells of a Gene from *Streptomyces alboniger* Conferring Puromycin Resistance", Nucleic Acids Research, 14: 4617-4624 (1986).
Southern et al., "Transformation of Mammalian Cells to Antibiotic Resistance with a Bacterial Gene Under Control of the SV40 Early Region Promotor", J. Mol. App. Genet., 1: 327-341 (1982).
Portela et al., "Oriented Synthesis and Cloning of Influenza Virus Nucleoprotein cDNA that Leads to its Expression in Mammalian Cells", Virus Research 4: 69-82 (1985).
Gluzman, "SV40-Transformed Simian Cells Support the Replication of Early SV40 Mutants", Cell, 23: 175-182 (1981).
Wigler et al., "DNA-Mediated Transfer of the Adenine Phosphoribosyltransferase Locus into Mammalian Cells", Proc. Natl. Sci. U.S.A., 76: 1373-76 (1979).
Vara et al., "Biosynthesis of Puromycin by *Streptomyces alboniger*: Characterization of Puromycin N-Acetyltransferase", Biochemistry, 24: 8074-8081 (1985).
Colbere-Garapin et al., "A New Dominant Hybrid Selective Marker for Higher Eukaryotic Cells", J. Mol. Biol., 150: 1-14 (1981).

(List continued on next page.)

*Primary Examiner*—Richard A. Schwartz
*Assistant Examiner*—Richard C. Peet
*Attorney, Agent, or Firm*—Arnold, White & Durkee

[57] ABSTRACT

A drug resistant strain of *P.chrysogenum* has said drug resistance conferred by heterologous DNA, in particular a heterologous gene(s) under the control of a Penicillium control sequence(s). Drug resistance is especially to sulfonamides, or to trimethoprim or methotrexate by a gene derived from plasmid R388. A vector capable of conferring resistance to methotrexate or sulfonamide on *P.chrysogenum*, comprises at least one said resistance gene under the control of trpC controlling sequences.

12 Claims, 4 Drawing Sheets

OTHER PUBLICATIONS

Fallon et al., "Isolation and Characterization of Puromycin-Resistant Clones from Cultured Mosquito Cells", Somatic Cell Genetics, 8: 521–532 (1982).

Portela et al., "Regulation of Gene Amplification and Expression in Cells that Constitutively Express a Temperature Sensitive SV40 T-Antigen", Nucleic Acids Research, 13: 7913–27 (1985).

Portela et al., "A Primer Vector System that Allows Temperature Dependent Gene Amplification and Expression in Mammalian Cells; Regulation of the Influenza Virus NSI Gene Expression", Nucleic Acid Research, 13: 7959–77 (1974).

Ching-Juh Lai et al., "Mapping Temperature-Sensitive Mutants of Simian Virus 40: Rescue of Mutants by Fragments of Viral DNA", Virology, 60: 466–475 (1974).

Graham et al., "A New Technique for the Assay of Infectivity of Human Adenovirus 5 DNA", Virology, 52: 456–467 (1973).

Thoman, "Hybridization of Denatured RNA Transferred or Dotted to Nitrocellulose Paper", Methods in Enzymology, 100: 255–267 (1983).

Langridge et al., "Extraction of Nucleic Acids from Agarose Gels", Analytical Biochemistry, 103: 264–271 (1980).

Gorman et al., "High Efficiency DNA-Mediated Transformation of Primatic Cells", Science, 221: 551–553 (1983).

Boyer et al., "A Complementation Analysis of the Restriction and Modification of DNA in *Escherichia Coli*" J. Mol. Biol., 41: 459–472 (1969).

Schechtman et al., "Structure of the Trifunctional trp-1 Gene from *Neurospora crasse* and Its Aberrant Expression in *Escherichia coli*", J. Mol. App. Genet. 83–99 (1983).

Messing, J., "New M13 Vectors for Cloning", Meth. Enzymol., 101: 20–79 (1983).

Swegberg et al., Plasmid-Borne Sulfonamide Resistance Determinants Studied by Restriction Enzyme Analysis, 153 J. Bact. 1228–1237 (1983).

Swift et al., DNA Sequence of a Plasmid-Encoded Dihydrofolate Reductage, 181 Mol Gen Genet 441–447 (1981).

Fling et al., Monitoring of Plasmid-Encoded, Trimethoprim-Resistant Dihydrofolate Reductase Genes: Detection of a New Resistant Enzyme, 22 Antimicrobial Agents and Chemotherapy, 882–888 (1982).

Penalva et al., The Nucleotide Sequence of the trpC Gene from *Penicillium chrysogenum*, 15 Nucl. Acids Res., 1874 (1987).

Sanchez et al., Molecular Cloning and Characterization of the trpC Gene from *Penicillium chrysogenum*, 205 Mol Gen Genet, 248–252 (1986).

Sanchez et al., Tranformation in *Penicillium chrysogenum*, 51 Gene, 97–102 (1987).

Ware et al., Physical and Genetic Analysis of the Inc-W Group Plasmids R388, Sa and R7K, 7 Plasmid, 239 (1982).

Zolg et al., Characterization of a R Plasmid-Associated, Trimethoprim-Resistant Dihydrofolate Reductase and Determination of the Nucleotide Sequence of the Reductase Gene, 9 Nucleic Acids Research, 697 (1981).

UCLA Symposia on Molecular and Cellular Biology 34: 29–38, 69–82, 345–366, 390–403.

Stedman's Medical Dictionary, pp. 646, 1249.

Miyajima et al., Mol. and Cell Biology, 4(3): 407–414 (1984).

van Solingen et al., 1985 *J. Cellular Biochemistry*, Suppl C. Abstr 1576.

FUNGAL RESISTANCE MARKERS

The present application claims priority to foreign filed application G.B. 860502, filed Jan. 1, 1986. The present application is a continuing application of U.S. application Ser. No. 009,713, filed Feb. 2, 1987.

The present invention relates to drug-resistance genes useful as selection markers for P.chrysogenum.

Although transformation in P.chrysegenum with auxotrophic markers has previously been reported (Sanchez, F., et al "Transformation in P.Chrysegenum." Gene 51: 97-107 (1987) ), dominant resistance markers (universal for all strains) not requiring any particular mutation of the host strain, have not so far been described.

Sulfonamides (e.g. sulfamethoxazole) are structural analogues of p-aminobenzoic acid. As far as is known, they act as drugs by reducing the amount of synthesis of functional dihydrofolate.

Sulfonamides are active against bacteria, yeasts, protozoa and plants but not mammals, as folic acid is a vitamin requirement for mammals.

Methotrexate (MTX) and trimethoprim (Tp), structural analogues of dihydrofolic acid, inhibit the action of the enzyme dihydrofolic acid reductase (DHFR). This enzyme catalyzes the reduction of dihydrofolic acid to tetrahydrofolic acid (THF). THF is a coenzyme in 1-carbon transfer reactions (biosynthesis of purines, vitamins and amino acids) but, from the pharmacological viewpoint, its most important function is in the reaction whereby deoxyuridylate (dUMP) is converted to deoxythymidylate (dTMP). In this latter reaction THF acts not only as a coenzyme but also as a reductant, being oxidized to DHF, and THF must be regenerated via the DHFR-catalyzed reaction. Thus inhibition of DHFR leads then to a deficiency of dTMP and, accordingly, or inhibition of DNA synthesis.

Although MTX and Tp both inhibit DHFR, Tp has a several fold lower affinity for eukaryotic as opposed to bacterial DHFR, so MTX is the drug of choice for the inhibition of eukaryotic DHFR.

Plasmid mediated resistance to sulfonamides is widespread and in some instances this resistance is due to a new dihydropteroate synthetase specified by the plasmid (e.g. plasmid R 388 - Svedberg. G. et al "Plasmid-borne sulfonamide resistance determinants studied by restriction enzyme analysis." J. Bacteriol. 153: 1228-1237 (1983)).

At least two varieties of plasmid-specified DHFR have been described (Fling, M. E., et al "Monitoring of plasmid-encoded, trimethoprim-resistant dihydrofolate reductase genes: detection of a new resistant enzyme." Antimicrob. Agents Chemother. 22: 882-888 (1982) ). accounting for Tp/MTX resistances. Type II DHFRs are essentially totally insensitive to Tp or MTX. Plasmid R388 specifies type II DHFR.

Resistance to MTX has been used as a marker for vectors in eukaryotic organisms (yeast, Drosophila cells, mammalian cells). In several cases the DHFR gene used is the one present in pR388 where the original bacterial promoter has been removed and substituted by a promoter homologous to the eukaryotic organism used (Miyajima, A., et al. "Expression of plasmid R388-encoded type II dihydrofolate reductase as a dominant selective marker in Saccharomyces cerevisiae." Mol. Cell. Biol. 4: 407-414 (1984). Bourois, M. et al. "Vectors containing a prokaryotic dihydrofolate reductase gene transform Drosophila cells to methotrexate-resistance." EMBO J. 2: 1099-1104 (1983). O'Hare, K., et al. "Transformation of mouse fibroblasts to methotrexate resistance by a recombinant plasmid expressing a prokaryotic dihydrofolate reductase." proc. Natl. Acad. Sci. U.S.A. 78: 1527-1531 (1981) ).

P.chrysegenum is an industrially important filamentous fungus of the Ascamycetes family, and is used in particular in the commercial production of penicillins. Much research has been directed towards obtaining high-yielding strains by classical mutagenesis and brute-force selection.

It has now been found that it is possible to apply the techniques of molecular cloning to P.chrysegenum by the introduction of drug-resistance markers into the P.chrysegenum chromosome, or as satellite DNA. Thus, in a first aspect of the present invention, there is provided a drug resistant strain of P.chrysegenum wherein the said drug resistance is conferred by heterologous DNA, and a method of transformation using said resistance.

In the co-pending application (DK 515/87; EP 87300916.1; JP 21653/1987; U.S. 009713) examples of auxotrophic markers are given for P.chrysegenum, and the text thereof is incorporated herein by reference. Particularly, strains of E. coli containing the trpC gene have been deposited under the Budapest Treaty with the National Collection of Industrial Bateria, Scotland, on Mar. 14, 1986, and have the deposit numbers NCIB 12222 and NCIB 12223. These deposits correspond to pPctrpC1 and pPctrpC6, as described herein, and it should be appreciated that references to these plasmids include references to corresponding plasmids and derivatives as described in the co-pending application.

Using promoters and terminators associated with P.chrysegenum. such as are present in pPctrpC1 and pPctrpC6, it is possible to use exogenous DNA conferring drug resistance on other organisms, (heterologous DNA) in P.chrysegenum. Thus, resistance to any desired drug can be conferred upon P.chrysegenum by use of homologous control sequences with an appropriate exogenous resistance gene.

For example, it has been found that the resistance genes of plasmid R388 can be incorporated in vectors for P.chrysegenum to confer resistance to Tp and Su.

The sequence of the plasmid R388-dihydrofolate reductase gene has been published (Swift. G., et al "DNA sequence of a plasmid-encoded dihydrofolate reductase." Mol. Gen. 181: 441-5447 (1981). Zolg. J. W. et al "Characterization of a R plasmid-associated, trimethoprim-resistant dihydrofolate reductase and determination of the nucleotide sequence of the reductase gene" Nucl. Acids Res. 9: 697-710 (1981) ). Details concerning the determination of the plasmid R388-dihydropteroate synthetase gene, substitution of the original bacterial promoters in both genes by a promoter from P.chrysogenum, and frequencies of transformation of the different constructions, are described in the Examples.

The present invention will be further illustrated with reference to the following Figures and Examples in which:

FIG. 1. Shows the construction of an EcoRI cassette fragment containing the structural gene of DHFR from R388. o Sau3AI sites. ΔTaqI sites. Dotted box is open reading frame (ORF) of DHFR.

FIG. 2. Shows the nucleotide sequence of the EcoRI cassette fragment containing the DHFR gene from R388. ORF of the DHFR gene is boxed. AluI recognition sequences are underlined.

FIG. 3. Shows a physical map of pPctrpCl. Symbols are as follows: E EcoRI; H HindIII; Ha HaeIII; N NcoI; Ns NsiI; P PstI; S SalI; Sm SmaI; X XhaI. Box is the Sau3A fragment of P.chrysegenum DNA containing the trpC gene. Dotted box is the trpC ORF. p trpC promoter. t: trpC terminator. Single line represents pUC13.

FIG. 4. Shows the construction of pFS1 and pFS2. Light dotted box is the trpC ORF gene, dark dotted box is the Mtx$^r$ gene. Enzyme nomenclature and symbols are as in FIG. 3. ( ) represents the filled end of the corresponding restriction cut. A AluI.

FIG. 5. Shows a physical map of the 1.7 Kb BamHI fragment from R388 containing the dihydropteroate synthetase gene.

FIG. 6. Shows the construction of pML1 and pML2. Light dotted box is the trpC ORF, dark dotted box is Su$^r$ gene. Enzyme nomenclature and symbols are as in FIG. 3. ( ) represents the filled end of the corresponding restriction cut.

EXAMPLES

EXAMPLE 1

Vectors With The R388-Dihydrofolate Reductase Gene Under The Control Of The P.chrysogenum troC Promoter And Terminator Construction of an EcoRI cassette fragment containing the R388-dihydrofolate reductase gene The dihydrofolate reductase structural gene from plasmid R388 is 236 bp long, and is contained in a pvuII-EcoRI fragment of 1160 bp (Swift, G., McCarthy, et al "DNA sequence of a plasmid-encoded dihydrofolate reductase." Mol. Gen. Genet. 181: 441-5447 (1981). Zolg, J. W. et al "characterization of a R plasmid-associated, trimethoprim-resistant dihydrofolate reductase and determination of the nucleotide sequence of the reductase gene." Nucl. Acids Res. 9: 697-710 (1981)).

In order to obtain a fragment with the complete nucleotide sequence of the structural gene and where most of the 5' upstream sequences had been deleted, there was purified from the pvuII-EcoRI fragment a Sau3AI-EcoRI fragment of 278 bp containing 156 bp of the structural gene (3' end plus additional 122 bp) and the adjacent TaqI-Sau3A1 fragment of 84 bp containing the 5' 80 bp of the structural gene plus an additional 4 bp upstream from the initial ATG. The ligation of the two fragments enabled the reconstitution of the structural gene with TaqI-EcoRI ends. To obtain the cassette EcoRI fragment, two oligonucleotides were synthesized that, when reannealed, had EcoRI-TaqI ends. pUC13, digested with EcoRI and treated with phosphatase was mixed with the two fragments and the reannealed oligonucleotides, and ligase was added. E. coli DH1 competent cells were transformed with the mixture. Clones containing the appropriate construct were selected. FIG. 1 shows the construction of this EcoRI cassette, and the sequence is shown in FIG. 2.

An AluI fragment of the EcoRI cassette

The 378 bp EcoRI fragment was digested with AluI (see FIG. 2). A 284 bp fragment was separated by electrophoresis on polyacrylamide (pAA) gel and purified by extraction with 0.5 M ammonium acetate 1 mM EDTA.

P.chyrsegenum trpC promoter and terminator

The coding sequence of the P.chrysegenum trpC gene has been published (Sánchez. F. et al "The complete nucleotide sequence of the trpC gene from P.chrysegenum" Nucl. Acids Res. 15 1874 (1987). Plasmid pPctrpC1 (Sánchez, F., et al "Molecular cloning and characterization of the trpC gene from P.chrysegenum", Mol. Gen. Genet. 205: 248-252 (1986)) contains 350 bp upstream from the initial ATG of the trpC gene and 289 bp downstream from the stop codon. FIG. 3 shows a map of pPctrpCI where the relevant characteristics of this construct are shown. Plasmid pPctrpCl has been deposited (NCIB 12222).

There is a single HaeIII restriction site in the 5' 350 bp (other HaeIII sites are placed in pUC13, trpC gene and trpC terminator sequences), situated 2 bp upstream from the initial ATG. To obtain a fragment containing the promoter sequence of this gene an EcoRI-HaeIII fragment of 346 bp was purified from pPctrpCl.

A unique NsiI recognition sequence is present in pPctrpCl, 16 bp downstream from the stop codon. Plasmid pPctrpCl was digested with NsiI, the sticky ends converted to blunt ends by T4 DNA polymerase digestion and the linearized plasmid digested with EcoRI. Two fragments were thus obtained, one containing the promoter and trpC gene (2.6 Kb) and the other (3 Kb) containing the original vector (pUC13) plus the terminator sequence of the trpC gene. This latter fragment was separated from the 2.6 Kb by pAA gel electrophoresis and purified by extraction with 0.5 M ammonium acetate 1 mM EDTA.

Litigation of promoter, terminator and gene: vector pFS1

Fragments of the Mtx$^r$ gene (284 bp), trpC promoter (350 bp) and pUC13-trpC terminator (3 Kb) were mixed in a 1:1:1 molar ratio and treated with T4 DNA ligase. E. coli DH1 competent cells were transformed with the mixture and clones containing the appropriate sequence in the appropriate orientation were selected. The plasmid from one of these clones was named pFS1. FIG. 4 shows the construction and map of pFS1.

A vector containing the trpC and Mtx$^r$ markers: pFS2

A SmaI-XbaI fragment containing the sequence trpC promoter-Mtx$^r$ gene-trpC terminator was obtained from pFSl by digestion with the relevant enzymes. The XbaI sticky end was blunted, using Klenow polymerase, and the said fragment was ligated to SmaI-digested pPctrpCl. E. coli DHI competent cells were transformed with the Oixture and clones containing inserts were selected. All the clones analyzed contained the Mtx$^r$ gene with the same direction of transcription as the trpC gene. The plasmid from one of these clones was named pFS2. The construction and map of pFS2 are shown in FIG. 4.

EXAMPLE 2

Vectors With The R388-Dihydropteroate Synthetase Gene Under The Control of the P.chrysegenum trpC promoter and Terminator Sequence of the plasmid R388 dihydropteroate synthetase gene, and a DNA fragment containing the same plasmid R388 contains the dihydropteroate synthetase gene in a BamHI fragment of 1.7 Kb (Ward, J. M.

et al "Physical and genetic analysis of the Inc-W group plasmids R388, Sa and R7K." Plasmid 7: 239-250 (1982)). Analysis by subcloning of various subfragments expressing or not expressing sulphonamide resistance in E. coli, together with partial nucleotide sequence, indicate that the putative structural gene is located between a NcoI and an AvaI restriction site (FIG. 5). The larger NcoI-BamHI fragment of 1.15 Kb was used in subsequent constructs as the structural dihydropteroate synthetase gene.

P.chrysegenum trpC promoter and terminator pPctrpCI contains a single NcoI restriction site (CCATGG) overlapping the initial ATG of the trpC gene see FIG. 3, (Sánchez, F. et al "The complete nucleotide sequence of the trpC gene from P.chrysegenum" Nucl. Acids Res 15 1874 (1987)). It also contains a unique NsiI site 16 bp downstream from the stop codon of the gene. Thus digestion of pPctrpCI with NsiI (and converting the sticky ends to blunt ends using T4 DNA polymerase) followed by digestion with NcoI and purification of the larger fragment (3.35 Kb) resulted in the original vector pUC13 being linked to the promoter and terminator of the trpC gene.

Ligation of promoter, terminator and gene: pML1

The fragment thus obtained was ligated to the NcoI-BamHI fragment of the gene (where the BamHI sticky end was converted to a blunt end by Klenow polymerase). E. coli DH1 competent cells were transformed with the mixture and clones containing the construct were selected. Plasmid from one of these clones was purified and named pML1. The construction of pML1 and its map are shown in FIG. 6.

A vector containing the trpC and Su$^r$ markers pML2

A smaI-SalI fragment containing the sequence trpC promoter -Su$^r$ gen- trpC terminator. The SalI sticky end was converted to a blunt end and the fragment was ligated to SmaI-digested pPctrpCl. E. coli DH1 competent cells were transformed with the mixture and clones containing the desired construct were selected. All the clones analyzed contained the Su$^r$ gene with the same direction of transcription as the trpC gene. The plasmid from one of these clones was named pML2. FIG. 6 shows the construction and map of pML2.

EXAMPLE 3

Transformation of P.chrysegenum trp2 to MTX Resistance

P.chrysegenum trp2 has been deposited at the Commonwealth Mycological Institute under deposit number CMICC 3027092.

50 ml of semidefined medium supplemented with tryptophan (250 μg/ml) and indole (50 μg/ml) were inoculated with $10^5$ spores/ml and incubated at 28° C. for 44 h (shaking, 300 rpm). Mycelium was recovered by filtration, washed thoroughly with distilled water and resuspended in 1.2 M KCl (10 ml per gram of wet weight). Protoplasts were formed by incubation of this suspension with Novozym 234 (Novo Enzyme Industries, 20 mg per g of mycelium) at 28° C. for 4-5 hours with gentle shaking. protoplasts were separated from mycelial debris by filtration through glass-wool, pelleted by low-speed centrifugation (10 min. 800 g), washed with 1.2 M KCl and finally resuspended in 0.5 ml of 1.2 M KCl per gram of initial wet weight. At this point protoplasts were counted under the microscope and appropriate dilutions plated in MM supplemented with tryptophan (250 μg/ml) and indole (50 μ/ml) and in the same medium containing the osmotic stabilizer (1.2 M KCl). For transformation, protoplasts were pelleted by low-speed centrifugation, resuspended ($10^9$ protoplasts/ml) in 10 mM Tris-HCl, 10 mM CaCl$_2$, 1.2 M KCl, pH 8.0 and incubated for 10 minutes at 30° C. 0.1 ml samples were mixed with plasmid DNA and 2 ml of 30% PEG 6000, 10 mM CaCl$_2$, 1.2 M KCl, 10 mM Tris-HCl. pH 8.0 were added and the mixture incubated for 5 minutes at room temperature. After recovery by low-speed centrifugation, the protoplasts were resuspended in 1 ml of 1.2 M KCl.

The DNA used in these transformation experiments were plasmids pFS1 and pFS2.

For plating, samples of treated protoplasts were mixed with 5 ml of osmotically stabilized agar medium (see below) maintained at 50° C., and Petri dishes containing 30 ml of the medium were overlaid with the mixture. When selection was for methotrexate resistance, the drug (2625 μg) was present only in the overlay medium, the amount being calculated for a final concentration of 75 μg/ml in the total volume of medium.

Protoplasts transformed with pFS2 were plated on minimal medium containing the osmotic stabilizer (selection for trp$^+$ transformants), on minimal medium containing tryptophan, indole, the osmotic stabilizer and Mtx (selection for Mtx$^r$ transformants) and on minimal medium containing the osmotic stabilizer and Mtx (selection for double transformants trp$^+$, Mtx$^r$). Trp$^+$ transformants appeared at the usual frequency of 50 per μg, but, when these clones were assayed for the expression of Mtx resistance (by streaking on minimal medium containing 75 μg/ml of Mtx) only 4% expressed resistance. Mtx resistant transformants or double transformants appeared at a frequency of 0.6-6 per μg, consistent with the above result. All the Mtx resistant transformants were concomitantly trp$^+$.

Protoplasts transformed with pFS1 (lacking portions of the trpC gene) were only selected for Mtx resistance. They appeared at a frequency of 0.6 per μg.

Southern blot analysis of total DNA from transformants showed that those clones expressing Mtx resistance contained several copies of the transformant plasmid, integrated in a tandem fashion. Thus pFS1 and pFS2 readily transform P.chrysegenum trp2 to methotrexate resistance. The fact that selection for methotrexate results in several copies of the vector being integrated into the genome, although decreasing the frequency of transformation, means that any sequence inserted in this vector will be present in multiple copies in transformed clones. pFSI and pFS2 contain single restriction sites for the enzymes EcoRI, pstI, SmaI and XbaI not affecting any of the markers, making them available as cloning sites.

EXAMPLE 4

Transformation of P.chrysegenum ATCC 10003 to MTX Resistance

Protoplasts of the strain P.chrysegenum ATCC 10003 were prepared as described for the P.chrysegenum trp2 strain (Example 3) except that indole and tryptophan were omitted from the incubation medium.

The DNA used in transformation experiments were pFSI and pFS2. Selection for Mtx resistance was carried out by plating protoplasts on minimal medium containing the osmotic stabilizer and Mtx to give a final concentration of 75 μg/ml. Mtx resistant transformants appeared at a frequency of 1 per μg.

Thus vectors pFS1 and pFS2, in addition to the advantaqes indicated in Example 3, are able to transform a wild type strain of P.chrysogenum to Mtx resistance and, accordingly any P.chrysegenum strain sensitive to Mtx.

EXAMPLE 5

Transformation of P.chrysogenum trp2 to Su Resistance

Protoplasts were prepared as described in Example 3 and transformed with pML2.

For plating, samples of treated protoplasts were mixed with 5 ml of osmotically stabilized agar medium (see below) maintained at 50° C., and Petri dishes containing 30 ml of the medium were overlaid with the mixture. When selection was for sulfamethoxazole resistance, the drug (70 mg) was present only in the overlay medium, at a final concentration of 2 mg/ml of total volume.

Selection was for trp+ phenotype (by plating on minimal medium plus the osmotic stabilizer), for sulfamethoxazole resistance (by plating on minimal medium containing indole, tryptophan, the osmotic stabilizer and sulfamethoxazole) and for trp+ and sulfamethoxazole resistance (by plating on minimal medium containing the osmotic stabilizer and sulfamethoxazole). Trp+ clones appeared at the usual frequency of 50 per μg. When these clones were assayed for the expression of sulfamethoxazole resistance (by streaking on minimal medium containing sulfamethoxazole at a concentration of 2 mg/ml) about 35% expressed the resistance. Su resistant transformants, or double transformants, appeared at a frequency of 10-15 per μg, consistent with the above result. All the sulfamethoxazole resistant transformants were concomitantly trp+.

Protoplasts transformed with plasmid pML1 (lacking portions of the trpC gene) were only selected for Su resistance. They appeared at a frequency of 5 per μg.

Southern blot analysis of total DNA transformants showed that those clones expressing sulfamethoxazole resistance contained the tranformant plasmid. Thus pML1 and pML2 readily transform P.chrysegenum trp2 to sulfamethoxazole resistance. pML1 and pM12 contain single restriction sites for the enzymes EcoRI and SmaI that do not affect any of the markers, leaving them available as cloning sites.

EXAMPLE 6

Transformation of P.Chrysogenum ATCC 10003 to SU Resistance

Protoplasts were prepared as described in Example 4. The DNA used in transformation experiments were pML1 and pML2. Selection for sulfamethoxazole resistance was carried out by plating on minimal medium containing the osmotic stabilizer plus sulfamethoxazole at a concentration of 2 mg/ml. Clones expressing the resistance gene appeared at a frequency of 0.5 per μg.

Thus pM1 and pML2, in addition to the advantages indicated in Example 5, are able to transform a wild type strain of P.chrysogenum to sulfamethoxazole resistance and accordingly, any P.chrysogenum strain sensitive to sulfamethoxazole.

The plasmids were deposited at the National Collection of Industrial Bacteria in strains of E.coli DH1 on 23 Mar. 1987 as follows:

Strain AM949 containing p FS1 : NCIB 12436
Strain AM950 containing p FS2 : NCIB 12437
Strain AM951 containing p ML1 : NCIB 12438
Strain AM952 containing p ML2 : NCIB 12439.

We claim:

1. A drug resistant strain of *Penicillium chrysogenum* where drug resistance is conferred by a vector for *P.chrysogenum* carrying a sulfonamide, trimethoprim or methotrexate resistance gene operably linked to the promoter region of the trpC gene isolated from *P. chrysogenum*.

2. The strain of *Penicillium chrysogenum* according to claim 1 where the trpC gene is a trpC gene in pPctpCI or pPctrpC6.

3. The strain of *Penicillium chrysogenum* according to claim 1 or 2 where the resistance gene is derived from plasmid R388.

4. The strain of *Penicillium chyrsogenum* according to claim 1 or 2 where drug resistance is conferred to any one of the drugs sulfonamide, trimethoprim or methotrexate.

5. The strain of *Penicillium chrysogenum* according to claim 1 or 2 where drug resistance is conferred to more than one of the drugs sulfonamide, trimethoprim or methotrexate.

6. A vector for *Penicillium chrysogenum* conferring methotrexate resistance to *Penicillium chrysogenum* comprising at least one methotrexate resistance gene operably linked to a trpC gene promotor region is isolated from *Penicillium chrysogenum*.

7. A vector conferring trimethoprim resistance to *Penicillium chrysogenum* comprising at least one trimethoprim resistance gene operably linked to a trpC promoter region isolated from *Penicillium chrysogenum*.

8. A *Penicillium chrysogenum* vector conferring sulfonamide resistance in *Penicillium chrysogenum* comprising at least one sulfonamide resistance gene operably linked to a trpC promoter region isolated from *Penicillium chrysogenum*.

9. A plasmid selected from the group consisting of:
pFS1, NCLB 12436
pFS2, NCLB 12437,
pML1, NCLB 12437, and
pML2, NCLB 12439.

10. A strain of *Penicillium chrysogenum* transformed with more than one of the vectors of claim 9.

11. A method of conferring drug-resistance to *Penicillium chrysogenum* comprising conferring resistance to the drug sulfonamide, trimethoprim, or methotrexate to *Penicillium chrysogenum*, where the drug resistance is conferred through transformation with any of the vectors of claim 9.

12. A drug resistance strain of *Penicillium chrysogenum* where drug resistance is conferred by a vector of claim 9.

* * * * *

UNITED STATES PATENT AND TRADEMARK OFFICE
CERTIFICATE OF CORRECTION

PATENT NO. : 5,006,471
DATED : April 9, 1991
INVENTOR(S) : Sanchez et al.

It is certified that error appears in the above—identified patent and that said Letters Patent is hereby corrected as shown below:

In claim 2, column 8, line 18 delete "pPctpCI" and insert --pPctrpC1--

In claim 6, column 8, line 34 delete "is"

In claim 9, column 8, line 49 delete "pML1, NCLB "12437" insert --PML1, NCLB "12438"--

In claim 12, column 8, line 59 delete "resistance" insert --resistant--

Column 2, lines 7 and 37 delete "chrysegenum" and insert --chrysogenum--.

Column 2, line 8 delete "Ascamycetes" and insert --Ascomycetes--.

Column 4, line 1, delete "chyrsegenum" and insert --chrysogenum--.

Column 4, line 2, 3, 6, 9 and 61, delete "chrysegenum" and add --chrysogenum--

Column 4, line 52, delete "Oixture" and insert --mixture--.

UNITED STATES PATENT AND TRADEMARK OFFICE
CERTIFICATE OF CORRECTION

PATENT NO.  : 5,006,471

DATED       : April 9, 1991

INVENTOR(S) : Sanchez et al.

It is certified that error appears in the above-identified patent and that said Letters Patent is hereby corrected as shown below:

Column 5, lines 11, 17, 48, and 51, delete "chrysengenum" and insert --chrysogenum--.

Signed and Sealed this

Second Day of February, 1993

Attest:

STEPHEN G. KUNIN

*Attesting Officer*  Acting Commissioner of Patents and Trademarks